United States Patent
Yamada et al.

(10) Patent No.: US 6,861,549 B2
(45) Date of Patent: Mar. 1, 2005

(54) PRODUCTION METHOD OF 4'-BROMOMETHYL-2-CYANOBIPHENYL

(75) Inventors: Seiji Yamada, Kurashiki (JP); Ken Ishihara, Kurashiki (JP); Toshio Nakamatsu, Kurashiki (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/322,017

(22) Filed: Dec. 17, 2002

(65) Prior Publication Data

US 2003/0233009 A1 Dec. 18, 2003

(30) Foreign Application Priority Data

Jun. 12, 2002 (JP) ........................................ 2002-172016

(51) Int. Cl.$^7$ .......................................... C07C 255/50
(52) U.S. Cl. ..................................................... 558/425
(58) Field of Search ........................................ 558/425

(56) References Cited

U.S. PATENT DOCUMENTS

| | | | |
|---|---|---|---|
| 5,288,895 A | | 2/1994 | Bousset et al. |
| 5,621,134 A | * | 4/1997 | Katsura et al. ............. 558/425 |
| 6,111,114 A | * | 8/2000 | Salibeni et al. ............. 548/250 |
| 6,214,999 B1 | | 4/2001 | Biard et al. |

FOREIGN PATENT DOCUMENTS

| | | |
|---|---|---|
| EP | 0 253 310 A2 | 1/1988 |
| EP | 0 470 794 A1 | 2/1992 |
| EP | 0 470 795 A1 | 2/1992 |
| EP | 0 566 468 B1 | 10/1993 |
| EP | 0 709 369 A1 | 5/1996 |
| JP | 06-192170 | 7/1994 |
| JP | 06-298684 | 10/1994 |
| JP | 2002-088044 A | 3/2002 |
| WO | WO 98/46562 | 10/1998 |
| WO | WO 99/33788 | 7/1999 |

OTHER PUBLICATIONS

Carini et al., "Nanopeptide Angiotensin II Receptor Antagonists: The Discovery of a Series of N–(Biphenylylmethyl)imidazoles as Potent, Orally Active Antihypertensives," *Journal of Medicinal Chemistry*, 34 (8), 2525–2547 (1991).

* cited by examiner

*Primary Examiner*—Johann Richter
*Assistant Examiner*—Ebenezer Sackey
(74) *Attorney, Agent, or Firm*—Leydig, Voit & Mayer, Ltd.

(57) ABSTRACT

The present invention relates to a production method of 4'-bromomethyl-2-cyanobiphenyl, which includes reacting 4'-methyl-2-cyanobiphenyl with bromine in the presence of a radical initiator and an oxidant. According to the present invention, since bromine can be regenerated by reacting hydrogen bromide, which is by-produced with the progress of bromination, with an oxidant, inhibition of bromination by hydrogen bromide, coloring by bromine and the like can be prevented. Thus, 4'-bromomethyl-2-cyanobiphenyl useful as a starting material of pharmaceutical products can be produced industrially beneficially.

6 Claims, No Drawings

PRODUCTION METHOD OF 4'-BROMOMETHYL-2-CYANOBIPHENYL

TECHNICAL FIELD OF THE INVENTION

The present invention relates to an industrially advantageous production method of 4'-bromomethyl-2-cyanobiphenyl useful as a synthetic intermediate for pharmaceutical products.

BACKGROUND OF THE INVENTION

4'-Bromomethyl-2-cyanobiphenyl useful as a synthetic intermediate for pharmaceutical products, such as a compound having an anqiotensin II antagonistic action, is disclosed in EP0253310 and the like. Various production methods of 4'-bromomethyl-2-cyanobiphenyl have been heretofore reported.

JP-A-6-192170 describes a method for brominating 4-methylbiphenyl compound with a brominating agent, such as N-bromosuccinimide and the like, in a halogenated hydrocarbon solvent in the presence of an azobis-compound. However, this method uses expensive N-bromosuccinimide and the like as a brominating agent, and is industrially disadvantageous.

U.S. Pat. No. 5,621,134 (corresponding to EP0709369) describes a method for producing 4'-bromomethyl-2-cyanobiphenyl using economical bromine as a brominating agent in the presence of a radical initiator. However, this method uses an equimolar amount of bromine, thus by-producing hydrogen bromide. Because the by-produced hydrogen bromide inhibits bromination, further addition of a radical initiator is necessary to complete the reaction. Moreover, because bromine remaining in the reaction system colors the resulting product, further purification is necessary for industrial use.

JP-A-2002-88044 describes a method for removing by-produced hydrogen bromide from the reaction system, which comprises conducting the reaction described in the above-mentioned U.S. Pat. No. 5,621,134 (corresponding to EP0709369) under reduced pressure. However, this method requires special equipment for the reaction to be conducted under reduced pressure. In addition, equipment for treating hydrogen bromide gas, which is a strong acidic gas, is also necessary, and this method is not industrially advantageous. It is also an economically unbeneficial method, because one of the bromine atoms contained in bromine does not contribute to the reaction.

WO99/33788 describes a method comprising using, as a brominating agent, bromine produced by the reaction of aqueous hydrobromic acid with hydrogen peroxide and regenerating bromine by reacting hydrogen bromide, which is by-produced by bromination, with hydrogen peroxide. According to this method, however, 48% aqueous hydrobromic acid and 50% aqueous hydrogen peroxide need to be used, thereby increasing the amount of water in the reaction system, and volume efficiency becomes poor. In addition, highly concentrated aqueous hydrogen peroxide, which is dangerous in handling, needs to be used, and this method is not industrially advantageous.

SUMMARY OF THE INVENTION

It is therefore an object of the present invention to provide an industrially advantageous production method of 4'-bromomethyl-2-cyanobiphenyl.

The present inventors have conducted intensive studies in an attempt to solve the aforementioned problems, and found that a co-presence of an oxidant in the reaction of 4'-methyl-2-cyanobiphenyl with bromine in the presence of a radical initiator converts by-produced hydrogen bromide to bromine, as a result of which the reaction proceeds without being inhibited by hydrogen bromide. It has been further found that the use of 0.5 equivalent amount of bromine completes the reaction, thereby affording economical production of 4'-bromomethyl-2-cyanobiphenyl. Accordingly, the present invention provides the following.

(1) A production method of 4'-bromomethyl-2-cyanobiphenyl, which comprises reacting 4'-methyl-2-cyanobiphenyl with bromine in the presence of a radical initiator and an oxidant.
(2) The production method of the above-mentioned (1), wherein the oxidant is bromate or chlorate.
(3) The production method of the above-mentioned (1), wherein the oxidant is sodium bromate.
(4) The production method of any of the above-mentioned (1)–(3), wherein water is contained in the reaction system.
(5) The production method of the above-mentioned (4), wherein water is used in a catalytic amount.

DETAILED DESCRIPTION OF THE INVENTION

The present invention is explained in detail in the following. A synthesis scheme of the production method of the present invention is shown below.

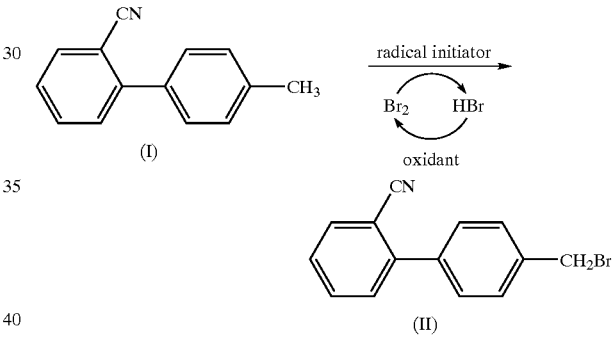

The present invention is achieved by, for example, reacting 4'-methyl-2-cyanobiphenyl represented by the formula (I) with bromine in a solvent in the presence of a radical initiator and an oxidant. While the order of addition of the reagents is not particularly limited, it is preferable that bromine or a solution thereof be added to a mixture of 4'-methyl-2-cyanobiphenyl, a radical initiator and an oxidant charged in a solvent in advance, from the aspect of operability. It is also possible to simultaneously add bromine, a radical initiator or a solution thereof. For smooth progress of the reaction, moreover, the reaction mixture is preferably placed under stirring.

In the present invention, the amount of bromine to be used is 0.4–0.7 mol, preferably 0.45–0.60 mol, more preferably 0.52–0.58 mol, per 1 mol of 4'-methyl-2-cyanobiphenyl, which is a starting material. When the amount of bromine to be used is less than 0.4 mol per 1 mol of 4'-methyl-2-cyanobiphenyl, the unreacted starting material tends to remain, and when it exceeds 0.7 mol, dibromo compound tends to be by-produced in a greater amount.

4'-Methyl-2-cyanobiphenyl, which is a starting material in the present invention, can be produced by a known method, such as a method described in J. Med. Chem. 1991, 34, 2525–2547, EP0470794, EP0470795, EP0566468 and the like.

As the radical initiator, azobis-compound, peroxide and the like are used. Specifically, the azobis-compound is exemplified by 2,2'-azobis(4-methoxy-2,4-dimethylvaleronitrile), 2,2'-azobisisobutyronitrile, 2,2'-azobis(2-methylbutyronitrile) and 2,2'-azobis(2,4-dimethylvaleronitrile); and peroxide is exemplified by dibenzoyl peroxide, di-t-butyl peroxide and the like. Preferred are 2,2'-azobis(2-methylbutyronitrile) and 2,2'-azobis (2,4-dimethylvaleronitrile), and particularly preferred is 2,2'-azobis(2-methylbutyronitrile).

The amount of a radical initiator to be used is 0.1–10 mol %, preferably 1–4 mol %, relative to 4'-methyl-2-cyanobiphenyl, which is a starting material. When the amount of a radical initiator to be used is less than 0.1 mol % relative to 4'-methyl-2-cyanobiphenyl, the reaction tends to be slow, and when it exceeds 10 mol %, the effect corresponding thereto is not obtained, which is industrially disadvantageous.

The oxidant is exemplified by oxidants whose handling is comparatively safe, such as bromates (e.g., sodium bromate, potassium bromate and the like); and chlorates (e.g., sodium chlorate, potassium chlorate and the like), with preference given to sodium bromate.

The amount of an oxidant to be used is an amount theoretically necessary for regenerating bromine from by-produced hydrogen bromide or a slightly excess amount thereof, which is 9–20 mol %, preferably 12–17 mol %, relative to 4'-methyl-2-cyanobiphenyl, which is a starting material. When the amount of the oxidant to be used is less than 9 mol % relative to 4'-methyl-2-cyanobiphenyl, bromine is not sufficiently regenerated and the yield tends to fall. When it exceeds 20 mol %, the effect corresponding thereto is not obtained, which is industrially disadvantageous.

The solvent to be used in the present invention is exemplified by halogenated hydrocarbon, alkane having 5 to 7 carbon atoms, aliphatic ester and the like. Specific examples thereof include methylene chloride, ethylene dichloride, carbon tetrachloride, monochlorobenzene, o-dichlorobenzene, bromobenzene, hexane, heptane, cyclohexane, methyl acetate, ethyl acetate, methyl propionate, ethyl propionate and the like. Of these, preferred are monochlorobenzene and ethyl acetate.

The amount of the solvent to be used is generally 0.5- to 20-fold weight, preferably 1- to 20-fold weight, more preferably 1- to 15-fold weight, most preferably 3- to 15-fold weight, relative to 4'-methyl-2-cyanobiphenyl, which is a starting material. When the amount is lower than this range, the effect of stirring tends to become poor, whereas an amount exceeding this range is industrially disadvantageous because the reaction tends to be slow and the like.

The reaction system in the present invention preferably contains water. The presence of water dramatically increases the effect of stirring, and makes the progress of the reaction smooth. The content of water is 0.01–50% (w/w), preferably 0.05–30% (w/w), relative to the solvent to be used. Even when the content of water is a catalytic amount (about 0.01–2.0% (w/w), preferably 0.05–0.5% (w/w), relative to the solvent to be used), the reaction proceeds sufficiently. When the content of water is less than 0.01% (w/w) relative to the solvent to be used, the effect of stirring tends to be not improved sufficiently, and when it exceeds 50% (w/w), the productivity tends to fall, which is not preferable for industrial production.

While the reaction temperature varies depending on the radical initiator and the like, it is generally 50–100° C., preferably 50–85° C., more preferably 60–85° C., most preferably 60–70° C. When the reaction temperature is lower than this range, the reaction tends to be slow, and when it is higher than this range, the reaction tends to be industrially meaningless because the radical initiator tends to become unstable and the like. The radical can be also produced by photoirradiation of radical initiator. In this case, a mercury lamp and the like can be used. The reaction time is also determined appropriately depending on the above-mentioned various reaction conditions (e.g., about 3–10 hr).

The 4'-bromomethyl-2-cyanobiphenyl obtained by the above-mentioned reaction is isolated and purified from a reaction mixture. The method therefor may be, but not limited to, a conventional method including removing inorganic salts by filtration and the like, distilling away the solvent as necessary, and recrystallizing from a different suitable solvent.

The 4'-bromomethyl-2-cyanobiphenyl obtained by the present invention can be introduced into a compound having an angiotensin II antagonistic action, according to the method described in, for example, EP0253310, JP-A-6-298684 and the like.

EXAMPLES

The present invention is explained in detail by referring to Examples, which are not to be construed as limitative.

Example 1

4'-Methyl-2-cyanobiphenyl (105 g, 0.54 mol) and sodium bromate (12.3 g, 0.082 mol) were added to monochlorobenzene (300 g) and the internal temperature was set for 65° C. 2,2'-Azobis(2-methylbutyronitrile) (2.0 g, 0.010 mol) was added, bromine (45.6 g, 0.29 mol) was added dropwise over 5 hr and the reaction mixture was maintained at this temperature for 1 hr. The resulting inorganic salt was filtered off and the reaction mixture was cooled to 5° C. The precipitated crystals were collected by filtration to give 4'-bromomethyl-2-cyanobiphenyl (110 g, 0.405 mol). The yield was 75%.

Example 2

In the same manner as in Example 1 except that 2,2'-azobis(2,4-dimethylvaleronitrile) (2.5 g, 0.010 mol) wa instead of 2,2'-azobis(2-methylbutyronitrile), the reaction and treatment were conducted to give 4'-bromomethyl-2-cyanobiphenyl (113 g, 0.416 mol). The yield was 77%.

Example 3

In the same manner as in Example 1 except that water (0.3 g) was added to monochlorobenzene (300 g), the reaction and treatment were conducted to give 4'-bromomethyl-2-cyanobiphenyl (114 g, 0.421 mol). The yield was 78%.

Example 4

4'-Methyl-2-cyanobiphenyl (105 g, 0.540 mol) and a solution of sodium bromate (12.1 g, 0.080 mol) in water (22.9 g) were added to monochlorobenzene (157.5 g) and the internal temperature was set for 80° C. 2,2'-Azobis(2-methylbutyronitrile) (2.0 g, 0.010 mol) was dissolved in monochlorobenzene (21 g) to give a solution (hereinafter Solution A) and ⅙ of Solution A was added. Then the remaining amount of Solution A and bromine (45.6 g, 0.287 mol) were dropwise added in parallel over 5 hr, and the mixture was maintained at 70° C. for 1 h. The aqueous layer was separated and removed, and the organic layer was cooled to 5° C. The precipitated crystals were collected by filtration to give 4'-bromomethyl-2-cyanobiphenyl (114 g, 0.416 mol). The yield was 78%.

Example 5

4'-Methyl-2-cyanobiphenyl (105 g, 0.540 mol) and a solution of sodium bromate (12.1 g, 0.080 mol) in water (25.4 g) were added to monochlorobenzene (105.0 g) and the internal temperature was set for 80° C. 2,2'-Azobis(2-methylbutyronitrile) (2.0 g, 0.010 mol) was dissolved in monochlorobenzene (21 g) to give a solution (hereinafter Solution A) and ⅙ of Solution A was added. Then the remaining amount of Solution A and bromine (45.6 g, 0.287 mol) were dropwise added in parallel over 5 hr, and the mixture was maintained at 70° C. for 1 h. The aqueous layer was separated and removed, and the organic layer was cooled to 5° C. The precipitated crystals were collected by filtration to give 4'-bromomethyl-2-cyanobiphenyl (114 g, 0.416 mol). The yield was 78%.

As the results above show, it was clarified that the co-presence of sodium bromate as an oxidant enabled bromination using bromine in an amount slightly exceeding a 0.5 equivalent amount of 4'-methyl-2-cyanobiphenyl, which is a starting material, in the Examples of the present invention.

According to the production method of the present invention, 4'-bromomethyl-2-cyanobiphenyl useful as a starting material of pharmaceutical products can be produced industrially beneficially.

Because the production method of the present invention is free of inhibition of bromination due to hydrogen bromide by-produced with the progress of bromination, the bromination is promoted, and the bromination can be completed without further addition of a radical initiator. Consequently, an advantage is afforded that only a trace amount of bromine remains in the reaction system, and the resulting product is not colored thereby.

Furthermore, since removal of hydrogen bromide, which is a strong acidic gas, from the reaction system or treatment thereof is not necessary, special equipment therefor is not necessary. In addition, two bromine atoms contained in bromine can be effectively utilized, which is economically beneficial. Moreover, because the amount of water to be added as necessary to the reaction system is comparatively small, the volume efficiency can be increased, and dangerous highly concentrated hydrogen peroxide solution is not necessary.

This application is based on a patent application No. 172016/2002 filed in Japan, the contents of which are hereby incorporated by reference.

What is claimed is:

1. A production method of 4'-bromomethyl-2-cyanobiphenyl, which comprises reacting 4'-methyl-2-cyanobiphenyl with bromine in a reaction system comprising a radical initiator and an oxidant selected from bromate and chlorate.

2. The production method of claim 1, wherein the oxidant is sodium bromate.

3. The production method of claim 1, wherein the reaction system further comprises water.

4. The production method of claim 2, wherein the reaction system further comprises water.

5. The production method of claim 3, wherein water is used in a catalytic amount.

6. The production method of claim 4, wherein water is used in a catalytic amount.

* * * * *